(12) United States Patent
Bernard et al.

(10) Patent No.: US 10,828,309 B2
(45) Date of Patent: Nov. 10, 2020

(54) DERMOCOSMETIC OR PHARMACEUTICAL USE OF A COMPOSITION COMPRISING AT LEAST ONE INHIBITOR OF SOME CHEMOATTRACTANT CYTOKINES

(71) Applicants: GREENPHARMA, Orléans (FR); CENTRE NATIONAL DE LA RECHERCHE SCIENTIFIQUE (CNRS), Paris (FR); UNIVERSITE DE STRASBOURG, Strasbourg (FR)

(72) Inventors: Philippe Bernard, La Ferté Saint-Aubin (FR); Dayana Abboud, Illkirch (FR); Jean-Luc Galzi, Weitbruch (FR); Nelly Frossard, Strasbourg (FR); Christelle Pillard, Orléans (FR); Quoc Tuan Do, Orléans (FR)

(73) Assignees: GREENPHARMA, Orléans (FR); CENTRE NATIONAL DE LA RECHERCHE SCIENTIFIQUE (CNRS), Paris (FR); UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 15/514,200

(22) PCT Filed: Sep. 22, 2015

(86) PCT No.: PCT/FR2015/000186
§ 371 (c)(1),
(2) Date: Mar. 24, 2017

(87) PCT Pub. No.: WO2016/046457
PCT Pub. Date: Mar. 31, 2016

(65) Prior Publication Data
US 2017/0296547 A1  Oct. 19, 2017

(30) Foreign Application Priority Data

Sep. 24, 2014 (FR) .................................. 14/02162

(51) Int. Cl.
| | | |
|---|---|---|
| *A61K 31/522* | (2006.01) | |
| *A61K 9/00* | (2006.01) | |
| *A61K 9/06* | (2006.01) | |
| *A61K 8/19* | (2006.01) | |
| *A61K 8/49* | (2006.01) | |
| *A61K 8/60* | (2006.01) | |
| *A61K 8/64* | (2006.01) | |
| *A61K 8/92* | (2006.01) | |

(Continued)

(52) U.S. Cl.
CPC .............. *A61K 31/522* (2013.01); *A61K 8/19* (2013.01); *A61K 8/34* (2013.01); *A61K 8/345* (2013.01); *A61K 8/368* (2013.01); *A61K 8/37* (2013.01); *A61K 8/44* (2013.01); *A61K 8/4913* (2013.01); *A61K 8/4926* (2013.01); *A61K 8/4953* (2013.01); *A61K 8/60* (2013.01); *A61K 8/64* (2013.01); *A61K 8/678* (2013.01); *A61K 8/922* (2013.01); *A61K 8/97* (2013.01); *A61K 9/0014* (2013.01); *A61K 9/0053* (2013.01); *A61K 9/06* (2013.01); *A61K 31/045* (2013.01); *A61K 31/047* (2013.01); *A61K 31/192* (2013.01); *A61K 31/198* (2013.01); *A61K 31/231* (2013.01); *A61K 31/355* (2013.01); *A61K 31/4015* (2013.01); *A61K 31/455* (2013.01); *A61K 31/7004* (2013.01); *A61K 31/7016* (2013.01); *A61K 33/38* (2013.01); *A61K 36/185* (2013.01); *A61K 36/28* (2013.01); *A61K 36/286* (2013.01); *A61K 36/73* (2013.01); *A61K 36/808* (2013.01); *A61K 36/8998* (2013.01); *A61K 38/018* (2013.01); *A61K 45/06* (2013.01); *A61K 47/14* (2013.01); *A61Q 19/00* (2013.01)

(58) Field of Classification Search
CPC .. A61K 31/045; A61K 31/047; A61K 31/192; A61K 31/198; A61K 31/231; A61K 31/355; A61K 31/4015; A61K 31/455; A61K 31/522; A61K 31/7004; A61K 31/7016; A61K 33/38; A61K 36/185; A61K 36/28; A61K 36/286; A61K 36/73; A61K 36/808; A61K 36/8998; A61K 38/018; A61K 8/19; A61K 8/34; A61K 8/345; A61K 8/368; A61K 8/37; A61K 8/44; A61K 8/4913; A61K 8/4926; A61K 8/4953; A61K 8/60; A61K 8/64; A61K 8/678; A61K 8/922; A61K 8/97; A61K 9/0014; A61K 9/0053; A61Q 19/00
See application file for complete search history.

(56) References Cited

U.S. PATENT DOCUMENTS

| | | | | |
|---|---|---|---|---|
| 4,833,147 A * | 5/1989 | Moeller | ................. | A61K 8/368 |
| | | | | 514/263.31 |
| 6,703,048 B1 * | 3/2004 | Bengs | ................. | A61K 9/1652 |
| | | | | 424/499 |
| 2008/0214641 A1 * | 9/2008 | Berger | ................. | C07D 231/56 |
| | | | | 514/405 |

OTHER PUBLICATIONS

Rad et al., "N7-Tosyltheophylline (TsTh): A Highly Efficient Reagent for the One-Pot Synthesis of N7-Alkyltheophyllines from Alcohols", online publication Mar. 25, 2014, Synthesis, vol. 46, pp. 1380-1388. (Year: 2014).*

(Continued)

*Primary Examiner* — Michael B. Pallay
(74) *Attorney, Agent, or Firm* — Browdy and Neimark, PLLC

(57) ABSTRACT

The present invention relates to the cosmetic or pharmaceutical use for a composition comprising a salicylic or nicotinic acid derivative inhibiting chemokines, for preventing or treating chronic internal and/or external inflammatory conditions.

13 Claims, 5 Drawing Sheets

(51) Int. Cl.

| | |
|---|---|
| *A61K 8/97* | (2017.01) |
| *A61Q 19/00* | (2006.01) |
| *A61K 45/06* | (2006.01) |
| *A61K 47/14* | (2017.01) |
| *A61K 8/34* | (2006.01) |
| *A61K 8/368* | (2006.01) |
| *A61K 8/37* | (2006.01) |
| *A61K 8/44* | (2006.01) |
| *A61K 8/67* | (2006.01) |
| *A61K 31/045* | (2006.01) |
| *A61K 31/047* | (2006.01) |
| *A61K 31/192* | (2006.01) |
| *A61K 31/198* | (2006.01) |
| *A61K 31/231* | (2006.01) |
| *A61K 31/355* | (2006.01) |
| *A61K 31/4015* | (2006.01) |
| *A61K 31/455* | (2006.01) |
| *A61K 31/7004* | (2006.01) |
| *A61K 31/7016* | (2006.01) |
| *A61K 33/38* | (2006.01) |
| *A61K 36/185* | (2006.01) |
| *A61K 36/28* | (2006.01) |
| *A61K 36/286* | (2006.01) |
| *A61K 36/73* | (2006.01) |
| *A61K 36/808* | (2006.01) |
| *A61K 36/8998* | (2006.01) |
| *A61K 38/01* | (2006.01) |

(56) References Cited

OTHER PUBLICATIONS

Seborrhoeic dermatitis, downloaded from https://en.wikipedia.org/wiki/Seborrhoeic_dermatitis on Aug. 20, 2019. (Year: 2019).*

Mohammad Navid Soltani Rad et al., "N7-Tosyltheophylline (TsTh): a highly efficient reagent for the one-pot synthesis of N7-alkyltheophyllines from alcohols", Synthesis, pp. 1380-1388, vol. 46, No. 10 (Mar. 2014).

S. Manzin et al., "Pharmacodynamic profile of isbufylline, a new antibronchospastic xanthine devoid of central excitatory actions", Arzneimittel-Forschung/Drug Research, pp. 1205-1213, vol. 40, No. 11 (Nov. 1990).

Vittorio Dal Piaz et al.,"Phosphodiesterase 4 inhibitors, structurally unrelated to Rolipram, as promising agents for the treatment of asthma and other pathologies", European Journal of Medicinal Chemistry, pp. 463-480, vol. 35, No. 5 (Feb. 2000).

Francesca Levi-Schaffer et al.,"Diethylene glycol monoethyl ether (Transcutol(R)) displays antiproliferative properties alone and in combination with xanthines",Skin Pharmacology, pp. 53-59, vol. 9 (Jul. 1996).

Clark et al., Diagnosis and Treatment of Seborrheic Dermatitis, American Family Physician, 91(3):185-190 (2015).

Seborrhoeic dermatitis, downloaded from https://en.wikipedia.org/wiki/Seborrhoeic_dermatitis on Aug. 20, 2019.

Berke et al., Atopic Dermatitis: An Overview, Atopic Dermatitis: An Overview, 86(1):35-42 (2012).

Tollefson et al., Atopic Dermatitis: Skin-Directed Management, American Academy of Pediatrics, 134(6):e1735-e1744 (2014).

Atopic dermatitis, downloaded from https://en.wikipedia.org/wiki/Atopic_dermatitis on Aug. 20, 2019.

* cited by examiner

DERMOCOSMETIC OR PHARMACEUTICAL USE OF A COMPOSITION COMPRISING AT LEAST ONE INHIBITOR OF SOME CHEMOATTRACTANT CYTOKINES

The present invention relates to the use of some derivatives inhibiting chemo-attractant cytokines (generally called chemokines), in cosmetic or pharmaceutical compositions. More precisely, the present invention relates to new applications of said derivatives of theophylline for treating chronic inflammatory diseases and allergic diseases; it is possible to mention in this regard, external chronic inflammatory diseases such as dermatoses (acne, atopic dermatitis, psoriasis, eczema, dry skin with atopic tendencies, skin rash . . . ) or internal such as Crohn's disease, allergic asthma and allergic rhinitis.

Crohn's disease is a chronic inflammatory bowel disease. The article of Grip O. and Janciauskiene S. (Atorvastatin reduces plasma levels of chemokine (CXCL10) in patients with Crohn's disease, PloS One, 2009, 4(5): e5263) shows the importance of chemokines in this pathology.

Allergic rhinitis is a chronic disease often linked to chronic dermatoses. An article of Takeuchi S. et al. (Changes in thymus- and activation-regulated chemokine (TARC) associated with allergen immunotherapy in patients with perennial allergic rhinitis. J Investig Allergol Clin Immunol, 2005, 15(3), 172-6) shows the involvement of chemokines in this pathology.

Dermatoses are skin and mucous membranes disorders, that are characterized by unsightly manifestations such as red patches and desquamation zones. Several pathologies are grouped under the name of dermatoses. We can cite, as non-limiting examples, eczema, atopic dermatitis, psoriasis, seborrheic dermatitis or acne. These dermatoses are very often the result of inflammatory phenomena and immune disorders.

In the case of atopic dermatitis, lesions are characterized by a severe dryness of the skin and by inflammatory lesions: papular, vesicular, squamous and very pruritic erythematous eruptions (itching). From a histological point of view, atopic dermatitis is characterized, as many dermatoses, by an infiltration of lymphocytes, monocytes and polynuclear eosinophils around the small vessels and the capillaries. From a biochemical point of view, it has been shown that chemokines are strongly involved in dermatoses and in chronic inflammatory diseases in general. For example, the article Saeki et al. (Thymus and activation regulated chemokine (TARC)/CCL17 and skin diseases, J Dermatol Sci, 2006, 43(2), 75-84) highlights the importance of the CCL17 chemokine in atopic dermatitis. Another article of Vestergaard et al. (Overproduction of Th2-specific chemokines in NC/Nga mice exhibiting atopic dermatitis-like lesions, J Clin Invest, 1999, 104(8), 1097-105) highlights the importance of the same CCL17 chemokine in skin diseases.

Chemokines are a family of small proteins, mostly soluble, of 8-14 kD. Their most studied function is the attraction and control of the activation state of the cells of the immune system. Some chemokines have proven to be good therapeutic targets for treating internal and external chronic inflammatory diseases in humans or animals.

The present invention shows new cosmetic, pharmaceutical and veterinary applications of some agents effective for directly inhibiting chemokines and treating chronic inflammatory diseases in human or animals. In this patent application, the generic term "pharmaceutical" is used for defining a product intended for use in humans as well as a product for intended for use in animals.

The invention relates to the use of a dermocosmetic or pharmaceutical composition for treating chronic inflammatory diseases of the human or animal skin, characterized in that said composition contains, in a pharmaceutically acceptable vehicle, an effective amount of at least one active agent having the general formula (I):

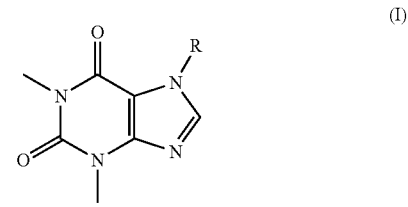

wherein:
R represents a ($C_1$-$C_6$) alkyl, a ($C_3$-$C_6$) cycloalkyl, ($C_2$-$C_6$) alkenyl group, the groups wherein one or more —$CH_2$— groups may be replaced by —O— or may be substituted by one or more radicals selected from ($C_1$-$C_6$) alkyl, hydroxy or alkoxy radicals, said compound of formula (I) may be in the form of a basic or acid addition salt.

Figure 10:
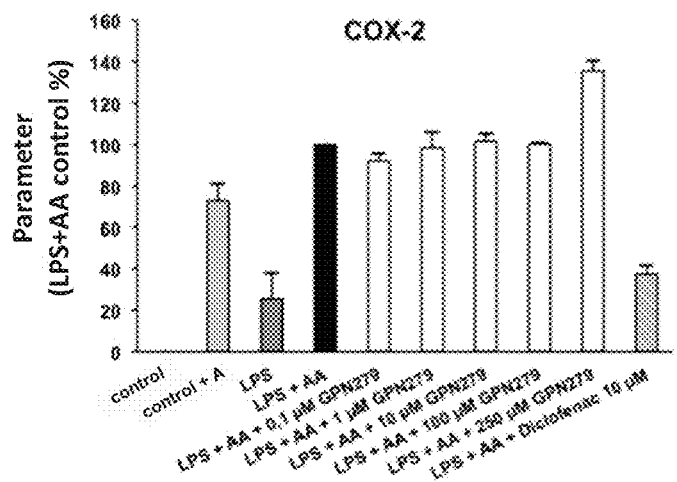

FIG. 10 shows the activity of COX-2(%) by determination of the production of PGE2 in monocytes incubated with LPS (10 U/ml), treated with GPN279 at 5 concentrations (0.1 µM, 1 µM, 10 µM, 100 µM, 250 µM) and arachidonic acid. Diclofenac (10 µM) is used as a cox-2 control inhibitor.

The compounds of formula (I) may possess one or more asymmetric centers and may then be isolated in an optically active form or in the form of their racemic mixture. The methods allowing to obtain optically active forms, for example by resolution of a racemic form or by synthesis using racemic starting products, are well known to one of ordinary skill in the art.

For the definition of the compounds of formula (I), the term "alkyl" refers to a linear or branched hydrocarbon radical advantageously having from 1 to 6 carbon atoms, such as methyl, ethyl, propyl, isopropyl, butyl, isobutyl, tert-butyl, pentyl, neopentyl, n-hexyl. The alkyl groups may be substituted by one or more hydroxyl groups and/or one or more alkoxy groups as defined hereafter.

The term "cycloalkyl" refers to a cyclic hydrocarbon system, comprising from 3 to 6 carbon atoms and that may be mono- or poly-cyclic. It is possible to mention in particular cyclopropyl and cyclohexyl radicals.

The "alkoxy" groups correspond to the linear or branched alkyl groups defined above linked via an —O— (ether) bond. The methoxy, ethoxy, n-propyloxy, i-propyloxy, n-butoxy, s-butoxy, t-butoxy, n-pentoxy and s-pentoxy are particularly preferred groups. The alkoxy groups may be substituted by an alkyl group as defined above or by another alkoxy group.

When in the composition implemented in the use according to the invention, the active agent is in the form of an acid addition salt, said acid is advantageously selected from the group consisting of hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methane- or ethane-sulfonic acid and camphoric acid.

When, in the composition implemented in the use according to the invention, the active agent is in the form of a basic addition salt, said base is advantageously selected from the group consisting of sodium or potassium hydroxide, triethylamine and tert-butylamine.

Among the compounds of formula (I) which may be used as active agent in the compositions implemented in the use according to the invention, it is possible to particularly mention:
3,7-dihydro-1,3-dimethyl-7-(3-methyl-2-butenyl)-1H-purin-2,6-dione also called prenyl-theophylline (coded GPN279)
3,7-dihydro-7-butyl-1,3-dimethyl-1H-purine-2,6-dione,
3,7-dihydro-7-isobutyl-1,3-dimethyl-1H-purine-2,6-dione,
3,7-dihydro-7-allyl-1,3-dimethyl-1H-purine-2,6-dione,
3,7-dihydro-7-(2-ethylhexyl)-1,3-dimethyl-1H-purine-2,6-dione.

The invention relates in particular to a use that implements a composition comprising at least one compound of formula (I) as active agent for treating inflammatory diseases of the skin. Such a composition may also comprise at least one active agent different from those of formula (I) for exerting at least one complementary or synergistic action.

According to another aspect of the invention, the composition implemented according to the invention is in the form of capsules, a cream, a gel, a lotion, a milk, an emulsion, a biphasic emulsion, an O/W or W/O emulsion, an unguent, a solution, an ointment, triphasic emulsions, a body oil, a shampoo, a nanocapsule, a liposome, a soap, a lip protective stick, a stick and pencil for makeup, masks, transdermic patches for topica applications.

In the form of a gel, the composition implemented according to the invention may comprise suitable excipients, such as cellulose esters, or other gelling agents, such as the carboxylic polymer "Carbopol®" and guar gum, for example.

In the form of emulsions, the composition implemented according to the invention have a good stability and may be stored for a required period of time for the use at temperatures between 0 and 50° C., without the constituents sedimenting or the phases separating.

According to another aspect of the invention, in the composition implemented according to the invention, the active agent(s) is (are) placed in encapsulation means selected from the group consisting of microspheres, liposomes, glycospheres, chylomicrons, macro-, micro and nanoparticles, macro-, micro- and nanocapsules.

According to another aspect of the invention, in the composition implemented according to the invention, the active agent(s) is (are) absorbed or adsorbed on powdery organic polymers, talcs, bentonite or other powdered mineral supports.

According to another aspect of the invention, in the composition implemented according to the invention, the content in active agent(s) of formula (I) is from 0.01% to 5% by weight with respect to the total weight of the composition.

According to another aspect of the invention, in the composition implemented according to the invention, the content in active agent(s) of formula (I) is (are) in encapsulated form and is from 0.5 to 5% by weight with respect to the total weight of the composition.

The invention notably relates to the use of a composition as previously defined for preventing and/or treating chronic inflammatory diseases whether internal, such as Crohn's disease, allergic asthma and allergic rhinitis, or external linked to seborrheic, acne, inflammatory and immunological activities; such composition may in particular be used for preventing and/or treating dermatoses, psoriasis, atopic dermatitis, as well as inflammatory conditions of the skin and hair systems causing chronic itching, irritation, redness or functional disorders of the capillary fragility.

The invention has thus shown the possibility of using the compounds of formula (I) as active agent(s). These compounds have very good properties for inhibiting some chemokines, such as CCL22 and/or CCL17.

The present invention therefore precisely aims at providing a new pharmaceutical, dermatological or cosmetic use implementing compositions which can treat internal and external chronic inflammatory diseases such as irritated, injured or sensitized skin by external or internal aggressions, in general, and in particular, dermatoses.

Thus, the present invention relates to a cosmetic use of at least one compound of formula (I) for inhibiting the CCL22 and/or CCL17 chemokine, for soothing dry skin with atopic tendencies and/or for improving and/or enhancing skin hydration. It therefore relates to uses for treating chronic inflammatory pathologies such as Crohn's disease, allergic rhinitis, allergic asthma, dermatoses such as atopic dermatitis, eczema and psoriasis.

In the therapeutic goal of the invention, the derivatives of formula (I) which can inhibit the CCL22 and/or CCL17 chemokine may be administered by the topical route but they may also be administered by the oral route. These derivatives may be used as such, in a liquid or powder form, purified or not.

Derivatives of formula (I) which can inhibit chemokines may, in the composition implemented, be associated with each other or with other compounds which complement the effect or even synergize this effect. The protective activity of the derivatives of formula (I) with respect to free radicals and UV-rays is interesting in the capillary field, in particular in the case of association with substances facilitating the good condition of the scalp and of the hair. It is possible to mention the associations with mucopolysaccharides, minerals, vitamins, ceramides, vegetal oils, antiradical substances, UV filters, flowers or fruits acids.

Similarly, the repairing activity of the compounds of formula (I) which can inhibit chemokines is particularly interesting when they are associated to substances having a healing effect such as proteins, hyaluronic acid, amino acids, or with anti-inflammatory, anti-aging, after-sun, anti-acne or anti-dermatosis substances.

As such, the composition implemented according to the invention are particularly adapted to a topical use for preventing and/or treating many skin defects, in particular as repairing and/or protective agents of the skin and the hair system such as the hair, for fighting against external aggressions linked to pollution, sun, oxidative stress, aging and skin pathologies leading to a dysfunction of epidermal or hair homeostasis.

These cosmetic compositions implemented according to the invention may also be in the form of lotions or solutions wherein compounds of formula (I) are in an encapsulated form, for example in microspheres. For example, these microspheres may be made of fat bodies, agar and water. The active agents may also be incorporated in vectors such as liposomes, glycospheres, chylomicrons, macro-, micro-, nanoparticles as well as macro-, micro and nanocapsules and may also be adsorbed on powdery organic polymers, talcs, bentonites and other mineral supports.

For the manufacture preparation of the compositions implemented according to the invention, the derivatives of formula (I) may be mixed with excipients generally used in cosmetics. The cosmetic compositions implemented according to the invention may therefore contain additives or adjuvants usual in cosmetology, as for example antibacterial agents or perfumes as well as extraction and/or synthesis lipids, gelling and viscosity polymers, surfactants, emulsifiers, hydro- or lipo-soluble active substances, plant extracts, tissue extracts, marine extracts, or synthesis active substances.

The dermo-cosmetic or pharmaceutical use of the compounds of formula (I) comprises all the body and skin care products, including sun products, for protection and tanning, anti-aging, anti-seborrheic, tonic products, products improving the appearance of the skin including the treatment of acne, the treatment of redness of the skin, the treatment of the scalp and that of hair loss.

The cosmetic compositions implemented according to the invention may also comprise other complementary active agents selected for their action, for example for sun protection, anti-wrinkles effect, antiradical and antioxidant activity, anti-irritant activity, cellular nutrition, respiration, hydration and regeneration, anti-seborrheic treatments, as well as other active agents having an action on skin tonicity and hair protection.

The cosmetic compositions implemented according to the present invention are preferably used daily by applying one or more times a day.

The cosmetic composition according to the present invention are very well tolerated, they present no phototoxicity and their application to the skin, for extended periods of time, does not lead to any systemic effect.

The invention also relates to the use of compounds of formula (I) for the manufacture of pharmaceutical compositions having an anti-inflammatory and/or dermoprotective activity. These compositions are in particular useful for preventing and/or treating dermatologic diseases linked to seborrheic, acne, inflammatory and immunological activities.

In summary, the invention therefore relates to the use of a pharmaceutical, dermatological or cosmetic composition, containing compounds of formula (I) which can inhibit some chemokines, for preventing and/or treating the pathologies or disorders resulting from:
natural or premature aging of the skin or hair;
dermatoses, such as psoriasis, acne and atopic dermatitis;
inflammatory and/or immunity conditions of the skin and hair systems, causing chronic itching, irritations, redness persistent irritations and itching, and functional disorders of the capillary fragility.

The present invention is now illustrated by the examples described hereafter.

Examples 1 to 5 illustrate methods for preparing derivatives of formula (I) which can inhibit the CCL17 and/or CCL22 chemokines according to the invention.

The starting products are commercially available or may be synthesized by classic methods known to one of ordinary skill in the art.

EXAMPLE 1

Synthesis of 3,7-dihydro-1,3-dimethyl-7-(3-methyl-2-butenyl)-1H-purin-2,6-diones or prenyl-theophylline (coded GPN279)

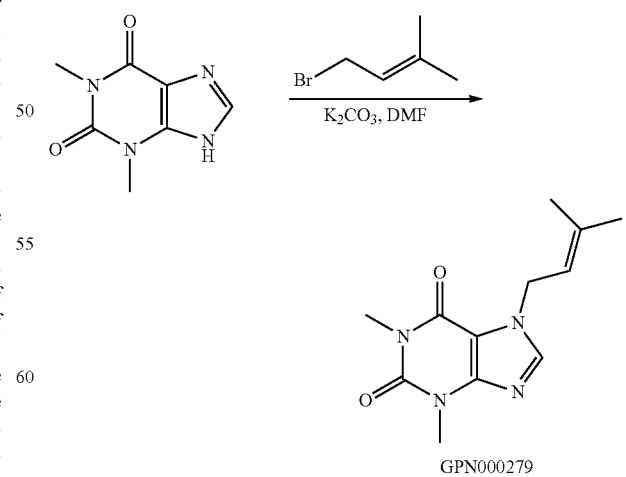

GPN000279

In a flask under argon, 2 g (0.0111 mol) of theophylline are dissolved in 30 mL of dimethylformamide, then 2.3 g (1.5 eq.) of potassium carbonate and 1.54 mL (1.2 eq.) of prenyl bromide are added. The reaction mixture is stirred for 18 hours at 40° C. then allowed to return to room temperature. It is poured onto ice water (approximately 40 mL) then extracted with ethyl acetate (3 times 30 mL). The combined organic phases are dried on magnesium sulfate, filtered and evaporated under reduced pressure. The crude is purified by silica gel chromatography (petroleum ether/ethyl acetate: 5/5, 3/7 then ethyl acetate alone) for obtaining 2.6 g of GPN279 (yield: 94%) in a form of a white solid.

RMN $^1$H (250 MHz, CDCl$_3$): δ 1.80 (s, 6H, 2 CH$_3$); 3.42 (s, 3H, NCH$_3$); 3.59 (s, 3H, NCH$_3$); 4.92 (d, 2H, J=7.25 Hz, CH$_2$); 5.44 (m, 1H, CH); 7.54 (s, 1H, CH).

RMN $^{13}$C (62.5 MHz, CDCl$_3$: δ 18.3 (CH$_3$); 25.8 (CH$_3$); 28.1 (NCH$_3$); 29.9 (NCH$_3$); 44.7 (CH$_2$); 107.2 (Cq); 117.9 (CH); 139.8 (Cq); 140.3 (CH); 148.9 (Cq); 151.8 (Cq); 155.5 (Cq).

EXAMPLE 2

Synthesis of 3,7-dihydro-7-butyl-1,3-dimethyl-1H-purine-2,6-dione (coded GPS008658)

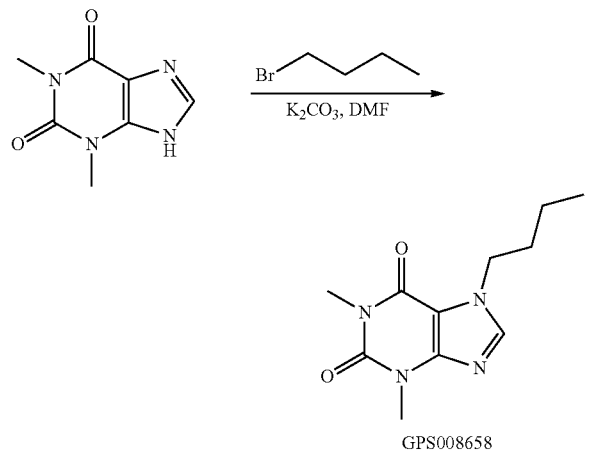

GPS008658

In a flask under argon, 0.200 g (1.1101 mol) of theophylline are dissolved in 3 mL of dimethylformamide, then 0.230 g (1.5 eq.) of potassium carbonate and 0.14 mL (1.2 eq.) of 1-bromutane are added. The reaction mixture is stirred for 18 hours at 40° C. then allowed to return to room temperature. It is poured onto ice water (approximately 10 mL) then extracted with ethyl acetate (3 times 10 mL). The combined organic phases are washed with a saturated sodium chloride solution, dried on magnesium sulfate, filtered and evaporated under reduced pressure. The crude is purified by silica gel chromatography (petroleum ether/ethyl acetate: 5/5 then 3/7) for obtaining 0.250 g of GPS008658 (yield: 95%) in a form of a white solid.

RMN $^1$H (400 MHz, CDCl$_3$): δ 0.96 (t, 3H, J=7.2 Hz, CH$_3$); 1.36 (sex, 2H, J=7.2 Hz, CH$_2$); 1.86 (q, 2H, J=7.2 Hz, CH$_2$); 3.42 (s, 3H, NCH$_3$); 3.60 (s, 3H, NCH$_3$); 4.29 (t, 2H, J=7.2 Hz, CH$_2$); 7.53 (s, 1H, CH).

RMN $^{13}$C (100 MHz, CDCl$_3$): δ 13.6 (CH$_3$); 19.7 (CH$_2$); 28.1 (NCH$_3$); 29.9 (NCH$_3$); 33.0 (CH$_2$); 47.2 (CH$_2$); 107.1 (Cq); 140.9 (CH); 149.0 (Cq); 151.8 (Cq); 155.3 (Cq).

EXAMPLE 3

Synthesis of 3,7-dihydro-7-isobutyl-1,3-dimethyl-1H-purine-2,6-dione (coded GPS008659)

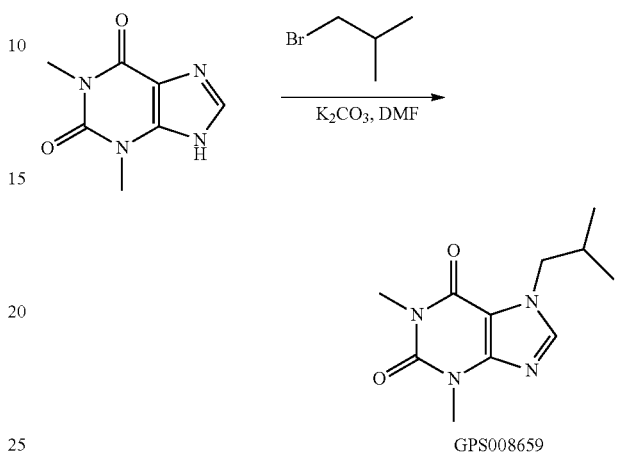

GPS008659

In a flask under argon, 0.200 g (1.1101 mol) of theophylline are dissolved in 3 mL of dimethylformamide, then 0.230 g (1.5 eq.) of potassium carbonate and 0.14 mL (1.2 eq.) of 1-bromo-2-methylpropane are added. The reaction mixture is stirred for 18 hours at 40° C. then allowed to return to room temperature. It is poured onto ice water (approximately 10 mL) then extracted with ethyl acetate (3 times 10 mL). The combined organic phases are washed with a saturated NaCl solution, dried on magnesium sulfate, filtered and evaporated under reduced pressure. The crude is purified by silica gel chromatography (petroleum ether/ethyl acetate: 5/5 then 3/7) for obtaining 94 mg of GPS008659 (yield: 35%) in a form of a white solid.

RMN $^1$H (400 MHz, CDCl$_3$): δ 0.94 (d, 6H, J=6.4 Hz, 2CH$_3$); 2.23 (sept, 1H, J=6.4 Hz, CH); 3.41 (s, 3H, NCH$_3$); 3.60 (s, 3H, NCH$_3$); 4.08 (d, 2H, J=7.2 Hz, CH$_2$); 7.50 (s, 1H, CH).

RMN $^{13}$C (100 MHz, CDCl$_3$): δ 19.7 (2CH$_3$); 28.1 (NCH$_3$); 29.8 (CH); 29.9 (NCH$_3$); 54.6 (CH$_2$); 107.3 (Cq); 141.3 (CH); 149.1 (Cq); 151.8 (Cq); 155.3 (Cq).

EXAMPLE 4

Synthesis of 3,7-dihydro-7-allyl-1,3-dimethyl-1H-purine-2,6-dione (coded GPS008660)

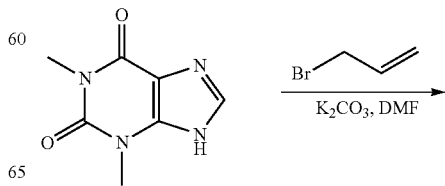

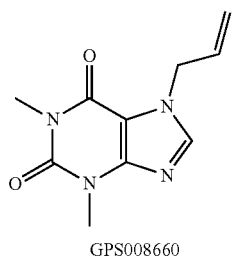

GPS008660

In a flask under argon, 0.200 g (1.1101 mol) of theophylline are dissolved in 3 mL of dimethylformamide, then 0.230 g (1.5 eq.) of potassium carbonate and 0.12 mL (1.2 eq.) of allyl bromide are added. The reaction mixture is stirred for 18 hours at 40° C. then allowed to return to room temperature. It is poured onto ice water (approximately 10 mL) then extracted with ethyl acetate (3 times 10 mL). The combined organic phases are washed with a saturated NaCl solution, dried on magnesium sulfate, filtered and evaporated under reduced pressure. The crude is purified by silica gel chromatography (petroleum ether/ethyl acetate: 5/5 then 3/7) for obtaining 230 mg of GPS008660 (yield: 94%) in a form of a white solid.

RMN $^1$H (400 MHz, CDCl$_3$): δ 3.41 (s, 3H, NCH$_3$); 3.60 (s, 3H, NCH$_3$); 4.95 (d, 2H, J=6.0 Hz, CH$_2$); 5.29 (dd, 2H, J=10.4 and 17.2 Hz, CH$_2$); 6.00-6.10 (m, 1H, CH); 7.57 (s, 1H, CH).

RMN $^{13}$C (100 MHz, CDCl$_3$): δ 28.1 (NCH$_3$); 29.9 (NCH$_3$); 49.1 (CH$_2$); 107.0 (Cq); 119.5 (CH2); 132.2 (CH); 140.8 (CH); 148.9 (Cq); 151.8 (Cq); 155.3 (Cq).

EXAMPLE 5

Synthesis of 3,7-dihydro-7-(2-ethylhexyl)-1,3-dimethyl-1H-purine-2,6-dione (coded GPS008661)

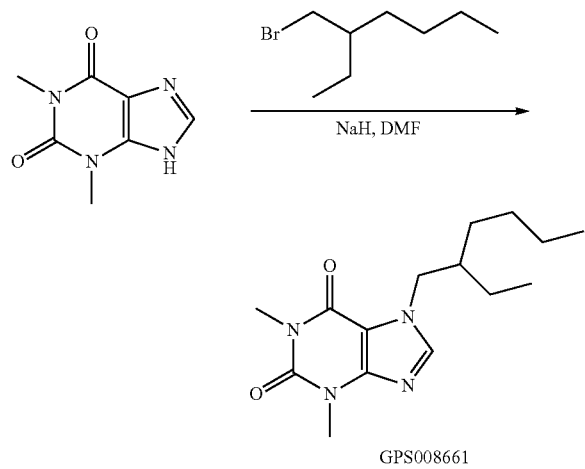

GPS008661

In a flask under argon, 0.400 g (2.2202 mol) of theophylline are dissolved in 10 mL of dimethylformamide, then 98 mg (1.1 eq.) of sodium hydride (60% in oil) are added. The reaction mixture is stirred for 10 minutes at room temperature then 0.52 mL (1.3 eq.) of 2-ethylhexyl bromide are added. The reaction is stirred for 2 days at room temperature, poured onto ice water (approximately 20 mL) then extracted with dichloromethane (3 times 20 mL). The combined organic phases are dried on magnesium sulfate, filtered and evaporated under reduced pressure. The crude is purified by silica gel chromatography (petroleum ether/ethyl acetate: 5/5) for obtaining 220 mg of GPS008661 (yield 34%) in a form of a colorless oil.

RMN $^1$H (250 MHz, CDCl$_3$): δ 0.86-0.94 (m, 6H, 2CH$_3$); 1.17-1.37 (m, 8H, 4CH$_2$); 1.89-2.02 (m, 1H, CH); 3.42 (s, 3H, NCH$_3$); 3.60 (s, 3H, NCH$_3$); 4.16 (d, 2H, J=7.5 Hz, CH$_2$); 7.49 (s, 1H, CH).

RMN $^{13}$C (100 MHz, CDCl$_3$): δ 10.4 (CH$_3$); 14.1 (CH$_3$); 23.1 (CH$_2$); 23.5 (CH$_2$); 28.2 (NCH$_3$); 28.4 (CH$_2$); 29.9 (NCH$_3$); 30.2 (CH$_2$); 40.1 (CH); 51.0 (CH$_2$); 107.3 (Cq); 141.4 (CH); 149.0 (Cq); 151.8 (Cq); 155.3 (Cq).

Example 6 shows the technical protocol allowing to record the effects of the products according to the invention on chemokines.

EXAMPLE 6

Inhibitory Properties of the Derivatives of Formula (I) on Chemokines.
Cells Expressing the CCR4 Receptor of Chemokines In order to enable an easy recording of the responses associated to the CCR4 receptor, the cDNA which allows its expression is cloned in the plasmid pIRES (ClonTech) in fusion with the GFP protein, according to Vollmer et al. (1999), which enables to easily measure the expression of the chimeric EGFP-CCR4 receptor. HEK 293 cells (ATCC) are cultured in minimal essential medium MEM (Invitrogen) in the presence of 10% of fetal calf serum (Gibco-BRL), 100 U/mL of penicillin (Invitrogen), 100 μg/mL of streptomycin (Invitrogen) and 2 mM of L-glutamine (Invitrogen) at 37° C. in water-saturated atmosphere and containing 5% of 002. The cells are transfected according to the calcium phosphate precipitate method of Chen ant Okayama, 1986, and the cells having incorporated the expression plasmid are selected with 600 μg/mL of geneticin G-418 (PAA) for 5 weeks. The clones are selected after having been characterized by fluorescence microscopy and cytometric analysis by FACS (fluorescence assisted cell sorting).
Construction of the Recombinant Protein Gqi5

In order to enable an easy recording of the cell responses associated to the CCR4 receptor, we modify its natural coupling to the inhibition of AMPc production to a coupling to the phospholipase C which enables calcium measurements. We produce for this purpose the chimeric protein Gqi5 by directed mutagenesis of the 5 las amino acids of Gq replaced by their homologues of Gi. The cells expressing the CCR4 receptor are transfected with the plasmid pCNA3.1 in which the cDNA encoding Gqi5 has been incorporated. The recordings of calcic responses are performed the day after de transfection.
Recording of Cell Calcium Responses and their Inhibition by the Molecules of the GPN Collection:

The cells are loaded with a fluorescent calcium indicator, INDO-1, according to the protocol provided by the provider (Molecular probes), distributed in microplate wells and placed in a fluorescence reader-pipettor (FlexStation, Molecular devices).

Intracellular calcium elevation is measured by fluorescence intensity change at 401 and 475 nm (excitation 355 nm). Measure points are recorded every 5 s for 150 s for each well. The molecules are tested in the presence of 5 nM of CCL17 chemokine (commercial).

Figure 1:
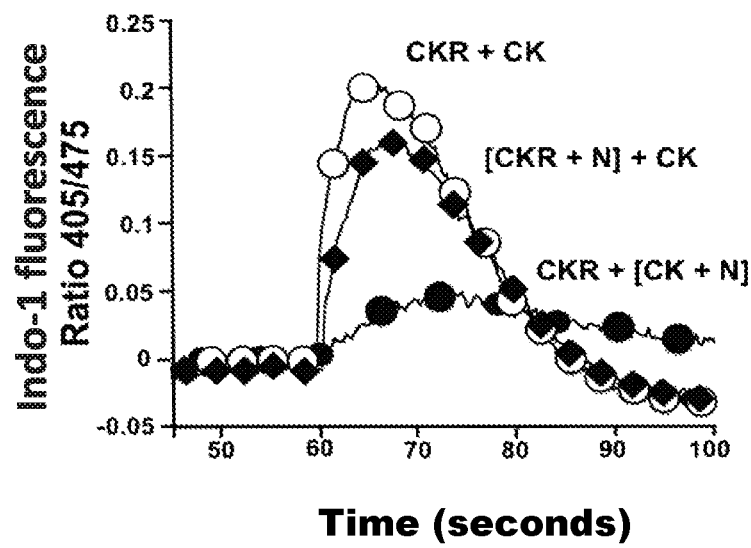
FIG. 1 represents the change in the ratio of fluorescence at 405 nm/475 nm of the calcic probe Indo-1 as a function of time expressed in seconds.

FIG. 1 shows in a general way the obtained results: the addition of chemokine (CK) to cells expressing the chemokine receptor (CKR) leads to a release of intracellular calcium revealed by the fluorescence change of the calcic probe Indo-1. The response develops in a few seconds and fades with time for reaching the return in approximately 2 minutes for a CCL17 chemokine concentration of 5 to 10 nM in HEK 293 cells expressing CCR4. If the molecules to be tested are preincubated with chemokine [CK+N] and if the mixture is added to the cells, we observe a strong decrease in the amplitude of the response if the molecule to be tested is a neutralizing ligand of the chemokine. Conversely, when the neutralizing ligand is preincubated with the cells expressing the receptor [CKR+N] we observe a much smaller decrease of the amplitude of the response.

This protocol has been used for identifying the neutralizing ligands of CCL17 presented in table 1.

Figure 2:
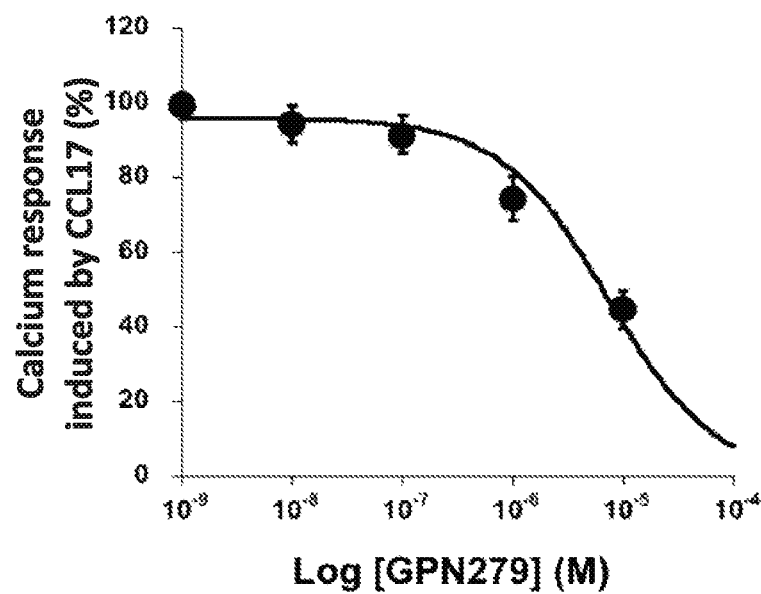
FIG. 2 represents the inhibition of the calcium response induced by CCL17 (5 nM), in percentage (%) as a function of the molar (M) concentration of GPN279 expressed as log [GPN279].

The apparent affinity of the GPN279 molecules is determined by the establishment of a dose-effect relationship of the inhibition of the calcium response as presented in FIG. 2 and the results obtained are reported in table 1.

TABLE 1

Table 1: structure/function relationships of the derivatives of formula (I)

| Cpd | Reference | Structure | Inhibition of calcium responses induced by CCL17 (%) | Inhibition of calcium responses induced by CCL22 (%) |
|---|---|---|---|---|
| 1 | GPN279 | 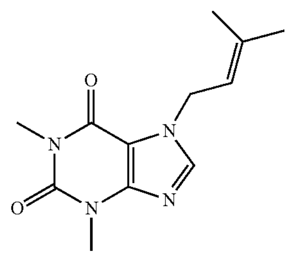 [SMILES: CC(C)=CCn1cnc2c1c(=O)n(C)c(=O)n2C] | 42 ± 4 | 0 |
| 2 | Theophylline | 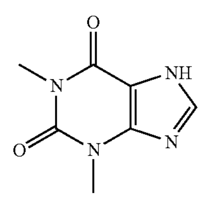 | 0 | 0 |
| 3 | Caffeine | 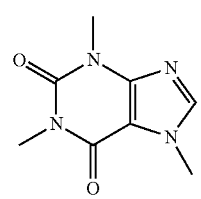 | 0 | 0 |
| 4 | GPN062 | 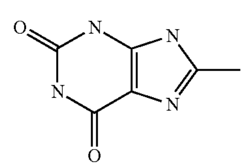 | 0 | 0 |
| 5 | IBMX | 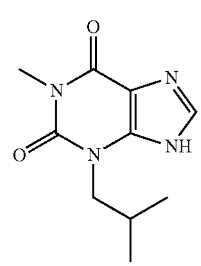 [SMILES: CC(C)Cn1c(=O)n(C)c(=O)c2nc[nH]c21] | 0 | 0 |

TABLE 1-continued

Table 1: structure/function relationships of the derivatives of formula (I)

| Cpd | Reference | Structure | Inhibition of calcium responses induced by CCL17 (%) | Inhibition of calcium responses induced by CCL22 (%) |
|---|---|---|---|---|
| 6 | GPS008658 | (structure) | 40 ± 9 | 32 ± 8 |
| 7 | GPS008659 | (structure) | 36 ± 7 | 5 ± 5 |
| 8 | GPS008660 | (structure) | 19 ± 5 | 0 |
| 9 | GPS008661 | (structure) | 0 | 0 |

The molecules are tested at the concentration of 10 μm. The concentration of CCL17 is 5 nM.

The analysis of the molecules selectivity is carried out by measuring the inhibition (at the concentration of 10 μm) of the response evoked by other chemokines (5 μm) on their respective receptors. Thus, in FIG. 3, the molecules have been tested on the pairs CCL2/CCR2, CCL3/CCR5, CCL17/CCR4, CCL22/CCR4, CXCL8/CXCR8, CXCL10/CXCR2, CXCL11/CXCR3, CXCL12/CXCR4.

Figure 3:
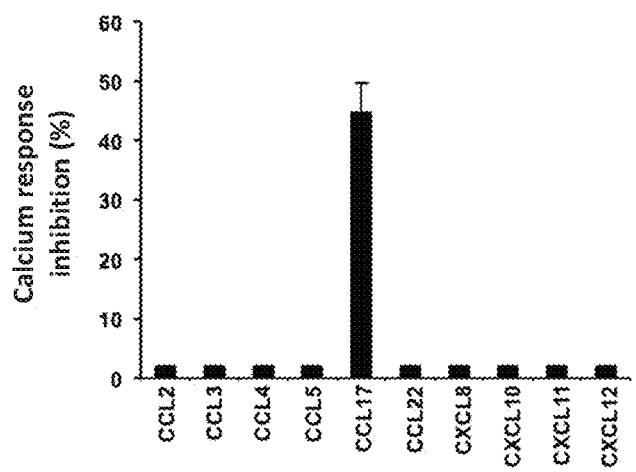
FIG. 3 represents the inhibition (at the concentration of 10 μm) of the calcium response, in percentage (%) induced by the following chemokines (at 5 μM) CCL2, CCL3, CCL17, CCL22, CXCL8, CXCL10, CXCL11, CXCL12.

FIG. 3 shows the selectivity of the neutralizing ligand of CCL17 (GPN1279) on the indicated chemokines and their respective receptors.

Determination of the Interaction Affinity of the Neutralizing Ligand of CCL17 by Fluorescence Extinction of Tryptophan Residues.

This measurement is carried out as described in Hachet-Haas et al. (Small neutralizing molecules to inhibit actions of the chemokine CXCL12, J Biol Chem, 2008, 283(34), 23189-99).

Briefly: the fluorescence measurements are carried out on a spectrofluorimeter Fluorolog 3 (JobinYvon/Spex) in a quartz cuvette. CCL17 (1.5 μm (HEPES buffer without albumin) in 1 mL final volume) is excited at 285 nm and its emission spectrum is recorded between 300 and 400 nm after each addition of an aliquot of molecule to be tested (1 μm). The measurements are carried out at 20° C. and the solutions are stirred using a magnetic stir bar. The recorded emission spectra are corrected by subtraction of the emission spectrum of the compound to be tested alone.

Figure 4:
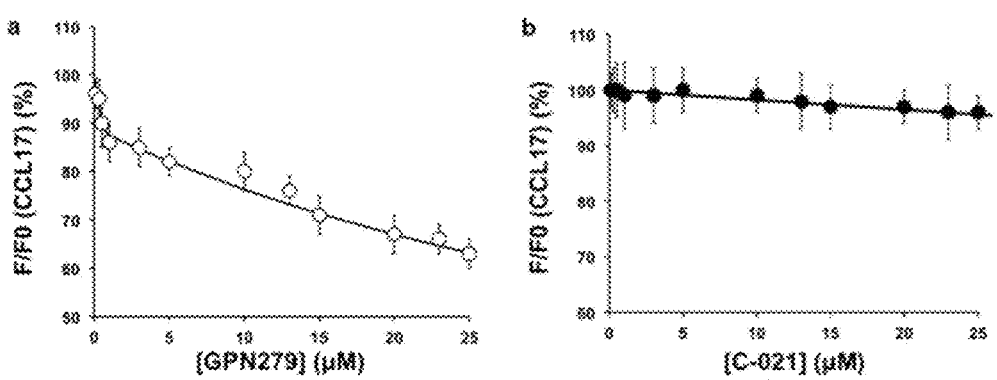
FIG. 4a shows the inhibition of the intrinsic fluorescence of CCL17, expressed in percentage (%), as a function of the concentration of GPN279 (in μM).
FIG. 4b shows the inhibition of the intrinsic fluorescence of CCL17, expressed in percentage (%), as a function of the concentration the CCR4 receptor antagonist C-021 (in μM).

FIG. 4 shows that a fluorescence extinction of CCL17 is observed with the neutralizing ligand (GPN 279) only and not with the CCR4 receptor's agonist (C-021 molecule). The shape of the titration curve of CCL17 (1.5 μm) by GPN 279 is biphasic, showing the plausible presence of several binding sites for GPN 279, at least one of which is of high affinity. The adjustment of the traces by the equation $(RL)^2+(RL)\times(-Ro-Lo-KD)+Ro\times Lo=0$ with $(RL)=((Ro+Lo+KD)\pm((-Ro-Lo-KD)^2-4\times Ro\times Lo)^{1/2})/2$ enables to establish the affinity for each site: KD<50 nM for the site of high affinity and KD=57 μm for the sites(s) of low affinity. There is no signal for the C-021 molecule.

FIG. 4a shows the inhibition of the intrinsic fluorescence of CCL17 by the neutralizing ligand GPN 279 (white circles). FIG. 4b shows that the CCR4 receptor antagonist, C-021, does not present a decrease of tryptophan fluorescence (black circles).

Example 3 allows showing how the noncytotoxic active candidates are selected.

EXAMPLE 3

Properties of the Derivatives on Keratinocytes Migration and Cytotoxicity

The activity of the GPN 279 molecule has been evaluated in a human keratinocytes migration assay performed according to an in vitro wound-healing test in a cell monolayer. It is actually known that, in chronic pathologies an important cell migration may promote de formation of pruritus, one of the signs of dermatosis. The immortalized human keratinocytes obtained from the DKFZ (Heidelberg, Germany) are cultivated in Dulbecco medium modified by Eagle (DMEM, Invitrogen) supplemented with 10% of fetal calf serum (Gibco-BRL) and 100 U/ml of penicillin (Invitrogen), 100 µg/ml of streptomycin (Invitrogen) and 2 mM of L-glutamine (Invitrogen) at 37° C. and 5% of CO2. The wells of a culture plate of 24 well are inoculated with 200,000 cells and the culture is maintained until formation of a confluent cell monolayer. The cell monolayer is then damaged by performing a linear gap (scratch) using a sterile pipette head of 0.1-10 µL. The medium is then replaced for eliminating the cells and their debris and the culture goes on in different experimental conditions: (i) without any addition, (ii) addition of 100 ng/ml of CCL17 and (iii) addition of a mixture containing 100 ng/ml of CCL17 and the molecule to be tested, for example GPN 279. The effect of the molecules alone is also recorded in different wells. In order to block cell proliferation, each well receives a dose of 1 µg/ml of mitomycin (Sigma-Aldrich). The culture plates are arranged in the IncuCyte apparatus (Essence Bioscience) which records the growth on the cell monolayer by transmitted imaging in cell culture conditions (37° C., 5% CO2, water-saturated atmosphere) for 72 h. Phase-contrast images are collected every 2 hours. Healing is defined (quantified) as the ratio of the width of the scar at time t and time 0. The experiment is repeated three times per condition. The obtained results are reported in FIG. 5.

Figure 5:
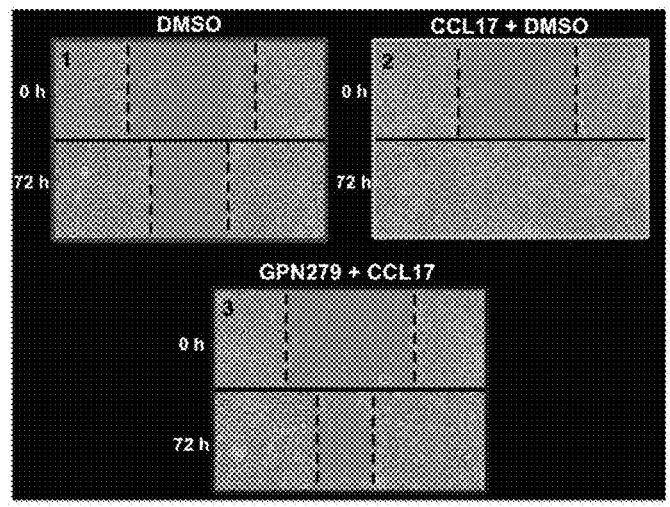
FIG. 5 shows pictures of monolayers of human keratinocytes (Hacat cells) after damage at time 0 and after 72 hours of culture in the presence of excipient alone (DMSO), CCL17 and excipient (CCL17+DMSO) and CCL17 and GPN279 (CCL17+GPN279).

FIG. 5 shows the migration of human keratinocytes under the effect of GNP279.

FIG. 5 shows pictures of monolayers of human Hacat cells after damage at time 0 and after 72 hours of culture in the presence of excipient alone (DMSO, table 1), CCL17 and excipient (CCL17+DMSO, table 2) and CCL17 and GPN1279 (CCL17+GPN279, table 3).

The figure shows that cell migration is greatly accelerated by the CCL17 chemokine which acts on the CCR4 receptors present in Hacat cells. This effect of the CCL17 chemokine is abolished by the GPN279 molecule.

Figure 6:
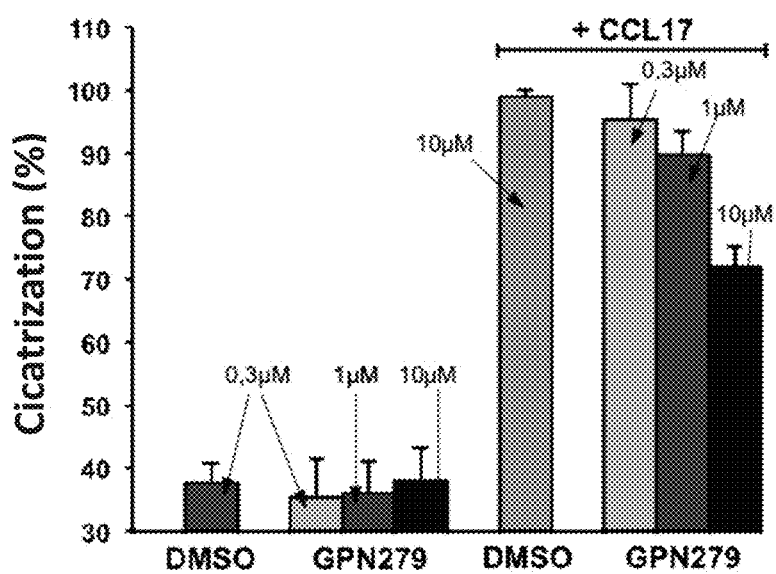
FIG. 6 shows the percentage (%) of healing in of the Hacat cell monolayer in presence of DMSO alone at 0.3 μM, GPN279 alone at 1 μM and 10 μM, DMSO+CCL17 at 10 μM, and GPN279+CCL17 at 0.3 μM, 1 μM, and 10 μM.

FIG. 6 shows the dose-response relationship of GPN279 on the Hacat cell monolayer healing, the GPN279 molecule alone does not have an effect and its effect depends on the dose (0.3 µM pink column; 1 µM violet column; 10 µM blue column).

Cytotoxicity Measurement

The metabolic activity test is a colorimetric test (WST-1 assay—Ozyme) based on the measurement of the activity of the mitochondrial enzyme succinate-tetrazolium reductase cleaving the tetrazolium salt WST-1 ((4-[3-(4-Iodophenyl)-2-(4-nitrophenyl)-2H-5-tetrazolio]-1,3 benzene disulfonate)) in a water-soluble derivative called formazan, a dye which absorbs light in the range of 420-480 nm. Hacat cells are distributed at the rate of 200.000 cells per well in a culture plate of 24 wells, in a final volume of 500 µL. They are cultured for 24 hours before adding mitomycin C (1 µg/ml) and the compound to be tested. The culture plate is incubated for 72 hours at 37° C., 5% CO2, in water-saturated atmosphere. The medium is then replaced by fresh medium supplemented with reagent WSR-1 then incubated for 2 hours at 37° C. The plates are stirred to homogenize the color in the wells and the absorbance is measured at 450 nm in the multiwell-plate reader. The measurements are carried out in triplicates. As enzymatic activity requires cellular integrity, the absorbance will be all the stronger as the metabolic state of the cells is good.

Figure 7:
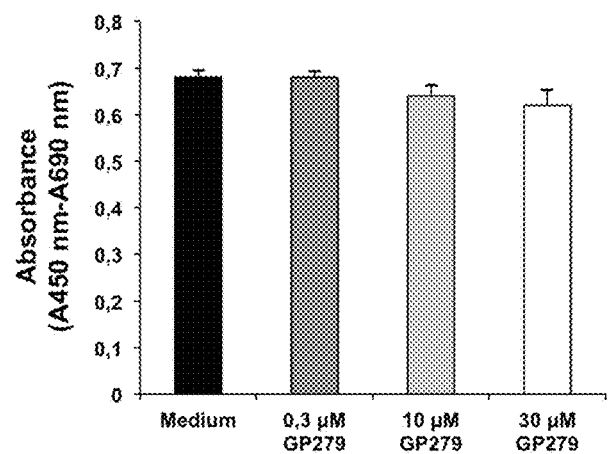
FIG. 7 shows the difference between the absorbance at 450 nm and the absorbance at 690 nm of Hacat cell cultures treated with medium or GPN279 at concentrations 0.3 μM, 10 μM or 30 μM.

In vitro cytotoxic activity: the Hacat cell cultures are treated with different concentrations of molecule: 0.3 µM (dark gray bars), 10 µM (light gray bars) or 30 µM (white bars) of the GPN279 molecule. The activity of the mitochondrial enzyme formazan-reductase is recorded using the chromogenic substrate WST-1 which turns into a colored product, called formazan, detected at 450 nm. As shown in FIG. 7, the GPN 279 molecule does not affect enzymatic activity.

EXAMPLE 7: GPN279 CYTOTOXICITY ON HUMAN MONOCYTES

Monocytes are inoculated in plates of 96 wells (approx. 5000 cells/well of 200 µl) for the Alamar blue assay. The cells are incubated with LPS (lipopolysaccharide) and GPN279 at 5 concentrations.

After 24 hours, Alamar blue fluorescence is measured.

Figure 8:
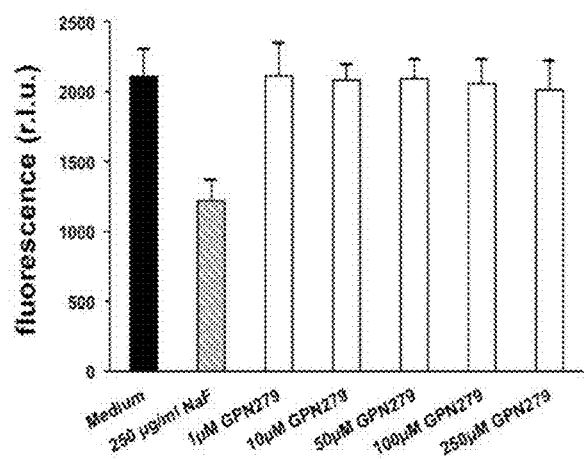
FIG. 8 shows the fluorescence (in relative luminescence unit (RLU)) of human monocytes which have been inoculated in 96 wells for the Alamar blue assay and incubated with lipopolysaccharide (LPS) and GPN279 at concentration of 1 μM, 10 μM, 50 μM, 100 μM and 250 μM in function of the dose of GPN279.

FIG. 8 shows the measurement of cytotoxicity by Alamar blue and indicates that GPN279 is not cytotoxic.

EXAMPLE 8: ABSENCE OF INHIBITION OF CYCLOOXYGENASES BY GPN279

The similarity of GPN279 with cyclooxygenase inhibiting compounds suggests that the possible mechanism could go through their inhibition. We show here that this is not the case.

Determination of the Activity of COX 1 and COX 2 Cyclooxygenases on Human Monocytes in Culture.

Figure 9:
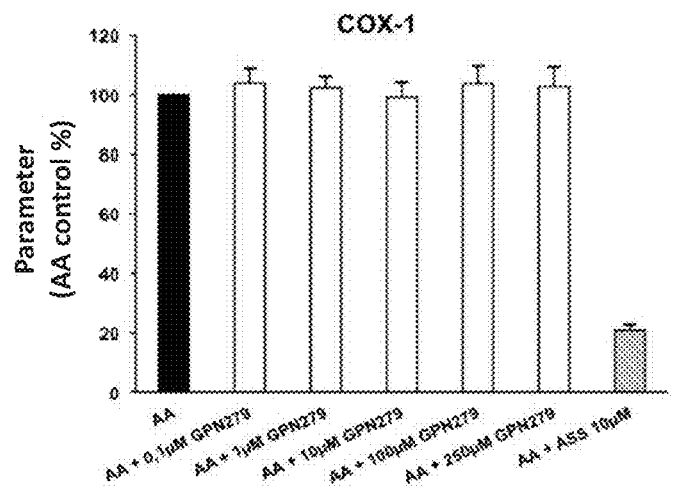
FIG. 9 shows the the activity of COX-1(%) by determination of the production of PGE2 in monocytes treated with arachidonic acid (AA) in the presence of GPN279 at 5 concentrations (0.1 µM, 1 µM, 10 µM, 100 µM, 250 µM). Aspirin (AS) a known inhibitor of COX-1 is used as a control inhibitor.

COX-1: the release of COX-1 mediated prostaglandin E2 (PGE2) is determined by the arachidonic acid method. The monocytes are treated with arachidonic acid (AA) in the presence of GPN279 at 5 concentrations which are added 15 min before arachidonic acid. After 15 minutes of stimulation, the activity of COX-1 is measured by determination of the production of PGE2. Aspirin (ASS) a known inhibitor of COX-1 is used as a control inhibitor. FIG. 9 indicates that GPN279 is not a COX-1 inhibitor at a concentration of up to 250 µM.

COX-2: monocytes are incubated with LPS (10 U/ml) for 24 h in order to induce COX-2 synthesis. After replacement of the culture medium (without serum), the cells are treated with GPN279 at 5 concentrations and diclofenac (10 µM) is used as a cox-2 control inhibitor. The arachidonic acid is added 15 minutes after the compounds to be tested, and 15 minutes later the production of PGE2 is determined.

FIG. 10 shows that GPN279 has no effect up to the dose of 100 µM, and induces a slight increase in COX-2 activity beyond.

EXAMPLE 9

This example presents a formulation of the composition according to the invention.

| COMMERCIAL NAME | INCI NAME | PERCENTAGE IN THE FORMULA |
|---|---|---|
| Simulsol 165 | PEG-100 Stearate/ Glyceryl Stearate | 3 |
| Montanov L | C14-22 Alcohol/C12-20 Alkyl Glucoside | 2 |
| Safflower oil | Carthamus Tinctorius Seed Oil | 2 |
| Shea butter | Butyrospermum Parkii Butter | 4 |
| Ceramidone | Octyldodecyl PCA | 3 |
| Phytosqualane | Squalane | 5 |
| DUB MCT 5545 | Caprylic/Capric Triglycerides | 7 |
| Beeswax | Cera Alba | 1 |
| Sorbic acid | Sorbic acid | 0.1 |
| Glycerin | Glycerin | 2 |
| Sorbitol | Sorbitol | 3 |
| Aristoflex AVC | Ammonium Acryloyldimethyltaurate/ VP copolymer | 1.3 |
| Xanthan gum | Xanthan gum | 0.2 |
| Nicotinamide | Niacinamide | 1 |
| Lipacide C8G | Capryloyl glycine | 0.5 |
| Purified water | Aqua | Qsp to 100 |
| GPN279 | — | 3 |

This composition is applied every day for one month to the skin of the face of a 20-year-old man suffering from atopic dermatitis over the whole face; this application consists in an application of 2 g/day for the whole face. A total progressive disappearance of the zones of inflammation is observed at the end of the treatment.

Ingredients which may be combined with the compositions for topic application in order to enhance the effect or reach action synergies have been proposed below, in particular with the formulation of the present example 6 (the amounts are given in percentage by weight):

a) ingredients having anti-inflammatory properties commonly used in cosmetic products, in particular nicotinamide (1 to 4%), 18 beta-glycyrrhetinic acid (0.01 to 1%), alpha bisabolol (0.1 to 1%);
b) glycine having a soothing effect (1 to 3%);
c) silver micro-particles (0.1%) which enable to regulate, stabilize the microbial flora and avoid superinfection;
d) an anti bacterial-adhesion agent for limiting adhesion and proliferation of Staphylococcus aureus such as Teflose® by Solabia group composed of propanediol, rhamnose, glucose and glucuronic acid (2 to 4%);
e) the unsaponifiables of shea butter and sunflower for strengthening the skin barrier and improving skin hydration (0.5 to 2%);
f) a chicory extract of 1 to 3% (such as Vederine® by Silab) for the reinforcement and recovery of the skin barrier;
g) a raspberry seed oil and vitamin E succinate derivative (Raspberry seed oil/Tocopheryl succinate/Aminopropanediol esters) at 1% such as Vitaskin® E by Solabia;
h) octyldodecyl PCA at 0.5 to 5% for stimulating the synthesis of epidermal lipids;
i) a safflower vegetable oil or stabilized evening primrose in a ceramide-like form such as "Omega 6 Ceramide® Safflower" and "Omega 6 Ceramide® Evening primrose" by Solabia for improving cell cohesion (0.1 to 1%)
j) an optimized mixture of argan oil, shea butter and barley wax, as in "Stimutex® AS" by DSM, for an anti-inflammatory action and for decreasing histamine release (2 to 5%);
k) a mixture of white birch bark and Scrophularia nodosa extract, as in Protectol® by Greetech, for its anti-inflammatory properties due to the presence of betulinic acid (1 and 3%);
l) a mixture of lactose and milk protein at 0.5% as in Modukine™ by CLR for its anti-inflammatory properties.

The invention claimed is:

1. A method for treating internal or external chronic inflammatory diseases in a human or animal individual, comprising administering to the individual a cosmetic or pharmaceutical composition comprising, in an acceptable vehicle, an effective amount of 3,7-dihydro-1,3-dimethyl-7-(3-methyl-2-butenyl)-1H-purin-2,6-dione or an addition salt thereof, as active agent, and wherein the diseases are chronic inflammatory diseases selected from the group consisting of atopic dermatitis, psoriasis, dry skin with atopic tendencies, Crohn's disease and allergic asthma.

2. The method according to claim 1, wherein the active agent is an acid addition salt, said acid being selected from the group consisting of hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartric acid, maleic acid, citric acid, ascorbic acid, methane- or ethane-sulfonic acid and camphoric acid.

3. The method according to claim 1, wherein the active agent is a basic addition salt, said base being selected from the group consisting of sodium or potassium hydroxide, triethylamine and tert-butylamine.

4. The method according to claim 1, wherein the composition comprises from 0.10% to 5% by weight of 3,7-dihydro-1,3-dimethyl-7-(3-methyl-2-butenyl)-1H-purin-2,6-dione or an addition salt thereof with respect to the total weight of the composition.

5. The method according to claim 1, wherein 3,7-dihydro-1,3-dimethyl-7-(3-methyl-2-butenyl)-1H-purin-2,6-dione or an addition salt thereof is in a form of powder, or is absorbed on powdery organic polymers, or is in an encapsulated form.

6. The method according to claim 5, wherein, when 3,7-dihydro-1,3-dimethyl-7-(3-methyl-2-butenyl)-1H-purin-2,6-dione or an addition salt thereof is in an encapsulated form, the encapsulation means is (are) selected from the group consisting of microspheres, liposomes, glycospheres, chylomicrons, macro-, micro and nanoparticles, macro-, micro- and nanocapsules.

7. A method according to claim 1, comprising administering to the individual a cosmetic composition, wherein the composition comprises at least one complementary active agent different than 3,7-dihydro-1,3-dimethyl-7-(3-methyl-2-butenyl)-1H-purin-2,6-dione or an addition salt thereof, said complementary agent being selected from the group consisting of sun-protection agents, anti-wrinkles agents with antiradical, antioxidant, anti-irritant activity, agents promoting cellular nutrition, respiration, hydration, regeneration, anti-seborrheic treatments, skin tone, hair protection, cicatrizing agents, hyaluronic acid, amino acids, anti-aging agents and after-sun agents.

8. The cosmetic method according to claim 7, wherein the composition is formulated in a form of lotion, gel, emulsion, cream or milk, triphasic emulsion, body oil, shampoo, mask, unguent, ointment, stick and pencil for makeup, nanocapsules, liposomes or transdermic patch for topic applications.

9. The cosmetic method according to claim 7, wherein the composition comprises at least one product selected from the group consisting of antibacterial agents, perfumes, extraction and/or synthesis lipids, gelling and viscosity polymers, surfactants, emulsifiers, plant extracts, tissue extracts, marine extracts, hydro- or lipo-soluble active substances, and synthesis active substances.

10. The method according to claim 1, wherein the composition comprises at least one product selected from the group consisting of mucopolysaccharides, vitamins, ceramides, vegetal oils and agents effective in dermatoses.

11. The method according to claim 1, wherein the composition is administrable by topical or oral route.

12. The method according to claim 1, wherein chemokines of the individual are inhibited.

13. The method according to claim 1, wherein 3,7-dihydro-1,3-dimethyl-7-(3-methyl-2-butenyl)-1H-purin-2,6-dione or an addition salt thereof is in a form of powder, or is absorbed on talcs or bentonites, or is in an encapsulated form.

* * * * *